(12) United States Patent
Doyle

(10) Patent No.: US 8,479,740 B2
(45) Date of Patent: Jul. 9, 2013

(54) AIRWAY DEVICES WITH INTEGRAL HUMIDIFICATION

(75) Inventor: Peter Doyle, Vista, CA (US)

(73) Assignee: Covidien LP, Mansfield, MA (US)

( * ) Notice: Subject to any disclaimer, the term of this patent is extended or adjusted under 35 U.S.C. 154(b) by 728 days.

(21) Appl. No.: 12/623,958

(22) Filed: Nov. 23, 2009

(65) Prior Publication Data

US 2011/0120468 A1    May 26, 2011

(51) Int. Cl.
*A61M 16/04* (2006.01)
*A61M 16/16* (2006.01)
*A62B 18/08* (2006.01)

(52) U.S. Cl.
USPC ............. 128/207.14; 128/201.13; 128/203.16

(58) Field of Classification Search
USPC ............. 128/203.16, 203.26, 207.14, 201.13; 604/6.14, 23–26
See application file for complete search history.

(56) References Cited

U.S. PATENT DOCUMENTS

| | | | |
|---|---|---|---|
| 4,488,548 A | 12/1984 | Agdanowski | |
| 4,495,948 A | 1/1985 | Shapiro | |
| 4,584,998 A | 4/1986 | McGrail | |
| 4,976,261 A | 12/1990 | Gluck et al. | |
| 5,313,955 A * | 5/1994 | Rodder | 600/538 |
| 5,752,921 A | 5/1998 | Orr | |
| 5,769,071 A | 6/1998 | Turnbull | |
| 5,794,986 A | 8/1998 | Gansel et al. | |
| 5,864,938 A | 2/1999 | Gansel et al. | |
| 6,315,739 B1 | 11/2001 | Merilainen et al. | |
| 6,576,034 B2 | 6/2003 | Berger | |
| 6,588,421 B1 | 7/2003 | Diehl et al. | |
| 6,596,049 B1 | 7/2003 | Berger | |
| 6,616,723 B2 | 9/2003 | Berger | |
| 6,725,862 B2 | 4/2004 | Klinberg et al. | |
| 6,739,339 B2 | 5/2004 | Bergamaschi | |
| 6,769,431 B2 * | 8/2004 | Smith et al. | 128/203.16 |
| 6,779,522 B2 * | 8/2004 | Smith et al. | 128/203.16 |
| 6,951,218 B2 | 10/2005 | Gradon et al. | |
| 6,961,600 B2 | 11/2005 | Kohl et al. | |
| 6,976,488 B2 | 12/2005 | Halperin | |
| 7,086,402 B2 | 8/2006 | Peterson | |
| 7,089,942 B1 | 8/2006 | Grey | |
| 7,107,991 B2 | 9/2006 | Kolobow | |
| 7,261,105 B2 | 8/2007 | Fukunaga et al. | |
| 7,418,965 B2 | 9/2008 | Fukunaga et al. | |
| 7,481,222 B2 * | 1/2009 | Reissmann | 128/207.14 |
| 7,503,328 B2 | 3/2009 | Kolobow et al. | |
| 2003/0062049 A1 | 4/2003 | Kolobow | |
| 2003/0196659 A1 | 10/2003 | Gradon et al. | |
| 2004/0245658 A1 * | 12/2004 | Niland et al. | 261/104 |

(Continued)

FOREIGN PATENT DOCUMENTS

WO     03028614     4/2003

OTHER PUBLICATIONS

Dupont Nafion PFSA Products Technical Information, NAE203, Nov. 2002, 2 pages.*

*Primary Examiner* — Justine Yu
*Assistant Examiner* — Douglas Sul (57) ABSTRACT

According to various embodiments, a tracheal tube may include an integral humidification system. The tracheal tube may be formed at least partially from a material that is permeable to water vapor but substantially impermeable to respiratory gases. The water vapor may be actively provided to the tracheal tube or may be passively transferred from a patient's surrounding airway space.

6 Claims, 8 Drawing Sheets

U.S. PATENT DOCUMENTS

| | | |
|---|---|---|
| 2004/0255952 A1 | 12/2004 | Carlsen et al. |
| 2005/0166924 A1 | 8/2005 | Thomas et al. |
| 2008/0029088 A1 | 2/2008 | Freitag |
| 2008/0078399 A1 | 4/2008 | O'Neil et al. |
| 2008/0078401 A1 | 4/2008 | O'Neil et al. |
| 2008/0078405 A1 | 4/2008 | Crumback et al. |
| 2008/0142003 A1 | 6/2008 | Depel |
| 2008/0216839 A1 | 9/2008 | Rutter |
| 2010/0083965 A1* | 4/2010 | Virr et al. ............... 128/203.26 |

* cited by examiner

AIRWAY DEVICES WITH INTEGRAL HUMIDIFICATION

BACKGROUND

The present disclosure relates generally to medical devices and, more particularly, to airway devices, such as tracheal tubes.

This section is intended to introduce the reader to aspects of the art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into the patient. For example, tracheal tubes may be used to control the flow of air or other gases through a patient's trachea. Such tracheal tubes may include endotracheal (ET) tubes, tracheotomy tubes, or transtracheal tubes. In many instances, it is desirable to provide a seal between the outside of the tube or device and the interior of the passage in which the tube or device is inserted. In this way, substances can only flow through the passage via the tube or other medical device, allowing a medical practitioner to maintain control over the type and amount of substances flowing into and out of the patient.

When a patient is ventilated through an artificial airway, normal mechanisms for moistening the airway (e.g., patient saliva and other secretions) are bypassed. Without humidification of the respiratory gases, the tissue in a patient's airway may become dry. Humidification of the respiratory gases delivered to the airway provides a substitute for the physiological processes that deliver moist air to the lungs, and allows the lungs and airway to retain appropriate levels of moisture.

BRIEF DESCRIPTION OF THE DRAWINGS

Advantages of the disclosure may become apparent upon reading the following detailed description and upon reference to the drawings in which.

DETAILED DESCRIPTION OF SPECIFIC EMBODIMENTS

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

A tracheal tube may be used to seal a patient's airway and provide positive pressure to the lungs. During mechanical ventilation, ventilator systems often draw respiratory gases from centralized hospital gas sources. These gases are typically stored in dry form to be used for a variety of purposes and, therefore, are commonly humidified prior to passing into a patient's airway system to more closely match the natural humidity of the patient's lungs. For example, ventilator systems may include a source of heated water that humidifies the gas as it passes through the tubing connecting the ventilator to the patient. However, such in-line humidification systems may be associated with certain drawbacks. Because the humidification may occur some distance away from the patient's airway, some of the humidity may be lost to the ventilation device as the humidified gas passes through the tubing. This in turn may prevent clinicians from accurately determining the humidity levels of the gas. Further, the tubing may become occluded with water droplets, preventing efficient transfer of the gas inside the tubing. In addition, the presence of water inside various connecting tubes that lead from the ventilator to the patient may present certain challenges for cleaning and/or replacing the tubes.

Provided herein are tracheal tubes that include integral humidification features that may provide more efficient humidification of gases passing into the lungs. Such tracheal tubes may include lumens or other passageways formed at least in part from a material that is permeable to water vapor but substantially impermeable to gases. Such a selectively permeable material may efficiently transfer heated water vapor into the tracheal tube without a loss of respiratory gases to the environment. In certain embodiments, the humidification features may include active humidification features, whereby the tracheal tubes are directly coupled to a source of heated water vapor. In such embodiments, the heated water vapor may be transferred through one or more lumens on the tube. The lumens are at least partially formed from the selectively permeable material, which allows water vapor to transfer out of the lumens to mix with the respiratory gases. In other embodiments, the humidification features may include passive humidification features, whereby the naturally humidified air of the upper respiratory tract is able to transfer into the tracheal tube through portions of the tube formed from or covered by the selectively permeable material. Because the selectively permeable material is substantially impermeable to respiratory gases, the pressure in the tracheal tube may be maintained. It should be understood that the passive and active humidification features may be used separately or together. Further, such systems may be used alone or in combination with other types of humidification features, such as in-line humidification or other types of humidification.

In embodiments described herein, the disclosed tracheal tubes, systems, and methods may be used in conjunction with any appropriate medical device, including without limitation a feeding tube, an endotracheal tube, a tracheotomy tube, a circuit, an airway accessory, a connector, an adapter, a filter, a humidifier, a nebulizer, nasal cannula, or a supraglottic mask/tube. The present techniques may also be used to treat any patient benefiting from mechanical ventilation, e.g., positive pressure ventilation. Further, the devices and techniques provided herein may be used to treat a human patient, such as a trauma victim, an intubated patient, a patient with a tracheotomy, an anesthetized patient, a cardiac arrest victim, a patient suffering from airway obstruction, or a patient suffering from respiratory failure.

Figure 1:
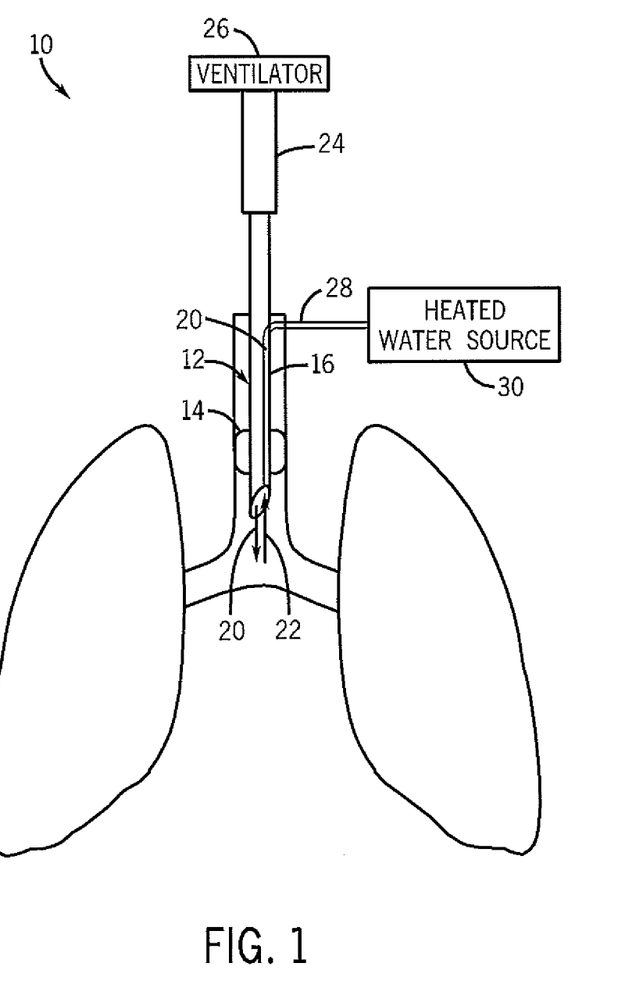
FIG. 1 illustrates an exemplary system including a tracheal tube with a humidification system.

FIG. 1 shows an exemplary tracheal tube system 10 that has been inserted into a patient's trachea. The system 10 includes a tracheal tube 12, shown here as endotracheal tube, with an inflatable balloon cuff 14 that is disposed on walls 16 of the tube 12 that may be inflated to form a seal against tracheal walls. The tracheal tube 12 is configured to deliver respiratory gases (represented by arrow 20) into the lungs and to allow the expiration of gases (represented by arrow 22) from the lungs. When mechanical ventilation is provided via the tube system, a ventilator 26 is typically provided, such as those available from Nellcor Puritan Bennett LLC. The ventilator 26 may be connected to the tube 12 through any appropriate configuration of connectors and/or tubing 24 for delivering respiratory gases 20 into the lungs.

As shown, the tracheal tube 12 may also include a humidification system for humidifying the gas 20 that is delivered to the lungs. The humidification system may be formed in or associated with the walls 16 of the tracheal tube 12. For example, the humidification system may include one or more lumens 28 or passageways formed in the wall 16 of the tube 12. At least part of the lumen 28 is formed from a selectively permeable material that allows water vapor from a water source 30, which in certain embodiments may be heated, to transfer into the passageway of the tube, as discussed below.

Figures 2, 3:
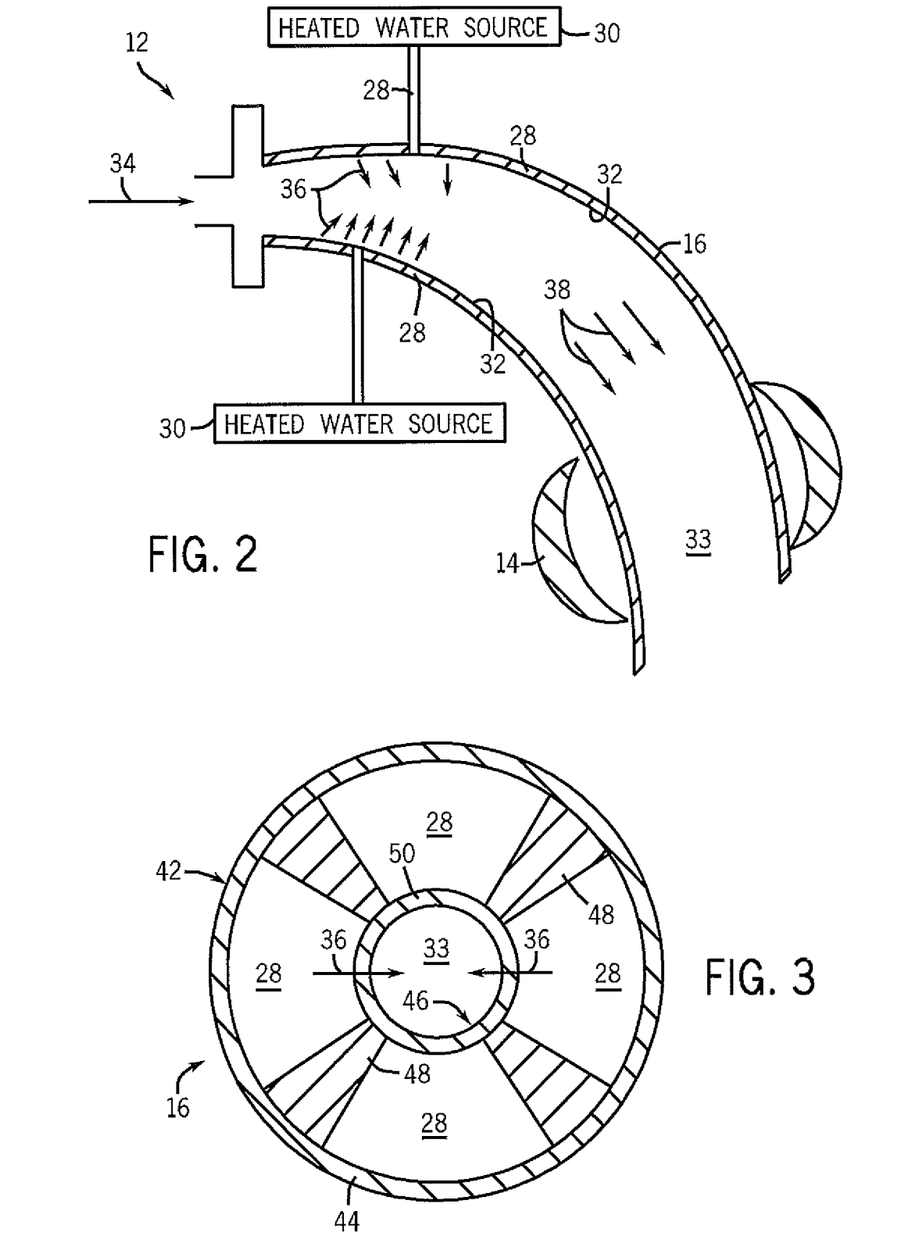
FIG. 2 is a cross-sectional view along an airway flow axis of an exemplary tracheal tube with an active humidification system including a selectively permeable material that is permeable to water vapor but substantially impermeable to gas.
FIG. 3 is a cross-sectional view orthogonal to the airway flow axis of a tracheal tube with a liner formed from a selectively permeable material.

FIG. 2 is a cross-sectional view of an exemplary tracheal tube 12 according to certain embodiments. During ventilation, dry gas, represented by arrow 34, from the ventilator 26 is transferred into the passageway 33 of the tube via transfer through interior surface 32, which faces the interior of the passageway 33. Moisture, represented by arrows 36, from the water source 30, which again may be heated, may mix with the dry gas to form heated/humidified gas, represented by arrows 38.

Diffusion through surface 32 may be achieved by forming at least part of the surface 32 from a material that is selectively permeable to water vapor but substantially impermeable to respiratory gases. The selectively permeable material (shown generically as material 50) allows water vapor to transfer (e.g., through proton exchange) directly into the tube 12. The transfer may be provided at a point as close as possible to the patient's airway and lungs to minimize loss of water vapor to the respiratory circuit. By forming all or part of the surface 32 from such material, the diffusion surface area may be controlled to allow a rate of diffusion of water vapor to achieve proper humidification of the respiratory gases.

Selectively permeable materials that are permeable to water vapor but substantially impermeable to respiratory gases may include proton exchange membranes formed from ionomers such as Nafion® (DuPont, Wilmington, Del.), polyaromatic polymers, or partially fluorinated polymers. Nafion® compounds are sulfonated fluoropolymers also known as perfluorocarbons, and may include a copolymer of at least two monomers with one monomer being selected from a group including vinyl fluoride, hexafluoropropylene, vinylidene fluoride, trifluoroethylene, chlorotrifluoroethylene, perfluoro(alkylvinyl ether), tetrafluoroethylene and mixtures thereof. Nafion® may be characterized by an equilibrium of ionic selectivity as well as transport properties. It is a perfluorinated polymer that contains small proportions of sulfonic or carboxylic ionic functional groups. Nafion® may be manufactured as a membrane or varying thickness or as sheet or tubing. Nafion® may be initially produced in a salt form with its sulfonic acid groups neutralized. In this form, Nafion® is thermoplastic (extrudable and formable using heat and pressure), but not chemically active.

Once provided in its final form (typically sheet or tubing), Nafion® may be chemically activated by conversion of the salt form to the acid form. At this stage, Nafion® is a translucent plastic that is similar in appearance to polytetrafluoroethylene, but clearer and less opalescent. Once activated, Nafion® immediately begins to react with its surrounding environment. Moisture is absorbed and exchanged with the surroundings. Reactive organic gas components within the surrounding air may undergo chemical changes when exposed to the super-acid catalytic activity of Nafion®.

The thickness and composite mixture of the selectively permeable materials may influence the transfer rate of water vapor. For example, thinner membranes may be associated with a higher rate of transfer. In addition, for materials that are copolymers or composites, the total percentage of the selectively permeable material in the composite may also be related to the transfer rate. It should be understood that the thickness and composition of the selectively permeable materials may be altered to change the rate of transfer of water vapor to a desired rate for humidifying respiratory gases. For example, respiratory gases may be humidified to at least 50% humidity, at least 80% humidity, or at least 95% humidity.

While all or a portion of surface 32 may be formed from a selectively permeable material, other portions of the tube 12, including portions of lumen 28, may be formed from materials that are substantially impermeable to both water vapor and respiratory gases (shown generically as material 44). Because all of the materials that form the respiratory circuit are substantially impermeable to the respiratory gases, which may represent a mix of gases as well as pharmacologic agents, the positive pressure achieved by mechanical ventilation may be maintained. The tube 12 and the cuff 14 may be formed at least in part from materials having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties such as Dow Pellethane® 2363-80A or polyvinyl chloride (PVC). The system 10 may also include a connecting tubing 24 connected to the endotracheal tube 12 that allows one-way flow of expired gases away from the patient and one-way flow of inspired gases towards the patient. Portions of lumen 28 connecting to a proximally located water source 30, the respiratory circuit, including the tube 12 and tubing/connectors 24, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene.

FIG. 3 is a cross-sectional view of a tube wall 16 of an exemplary configuration of tube 12 along an axis orthogonal to the airway passage 33. The tube 12 may include multiple lumens 28 that are formed in the walls 16 of the tube 12. The inside surface 32 of the walls 16 is a liner of a selectively permeable material 50 while the exterior surface 42 is formed of a material 44 substantially impermeable to water vapor and respiratory gases, as provided herein. The selectively permeable material 50 and the exterior wall structure formed of the impermeable material 44 are coupled together by support ribs 48 or other suitable support structures, which, in certain embodiments, may be selectively permeable or may be substantially impermeable to water vapor. The lumens 28 are coupled to a water source 30 and may allow transfer of water vapor 36 into the airflow passage 33 through the selectively permeable material 50.

The spacing, size, and number of support ribs 48 may determine the number and size of the lumens 28 formed between the selectively permeable material 50 and the exterior wall structure formed from material 44. Generally, it is envisioned that the lumens 28 may be formed so that the airway passage 33 is not substantially reduced in diameter, whereby the flow of air through the tube 12 is not substantially altered by the presence of the lumens 28.

Figure 4:
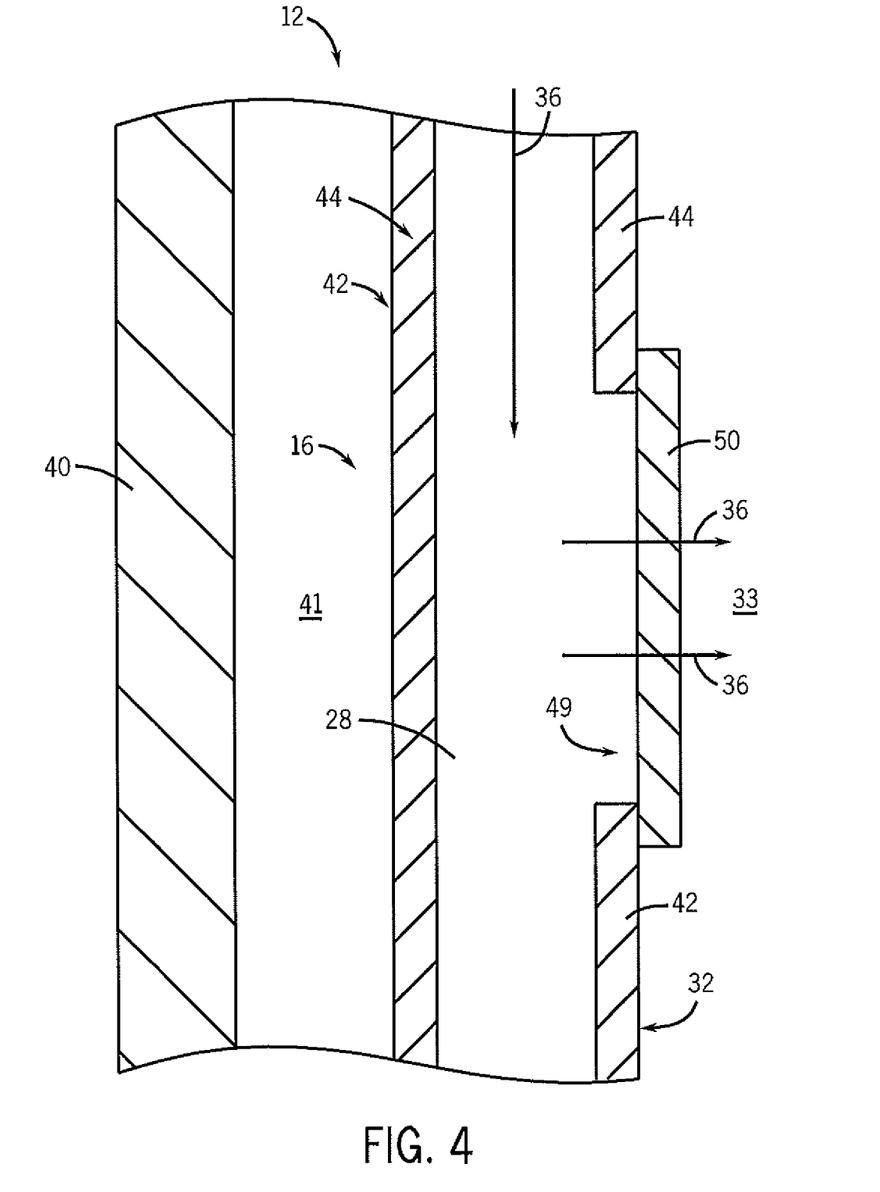
FIG. 4 is a cross-sectional view along an airway flow axis of an exemplary tracheal tube with one or more humidification lumens that include windows formed from a selectively permeable material.
Figure 5:
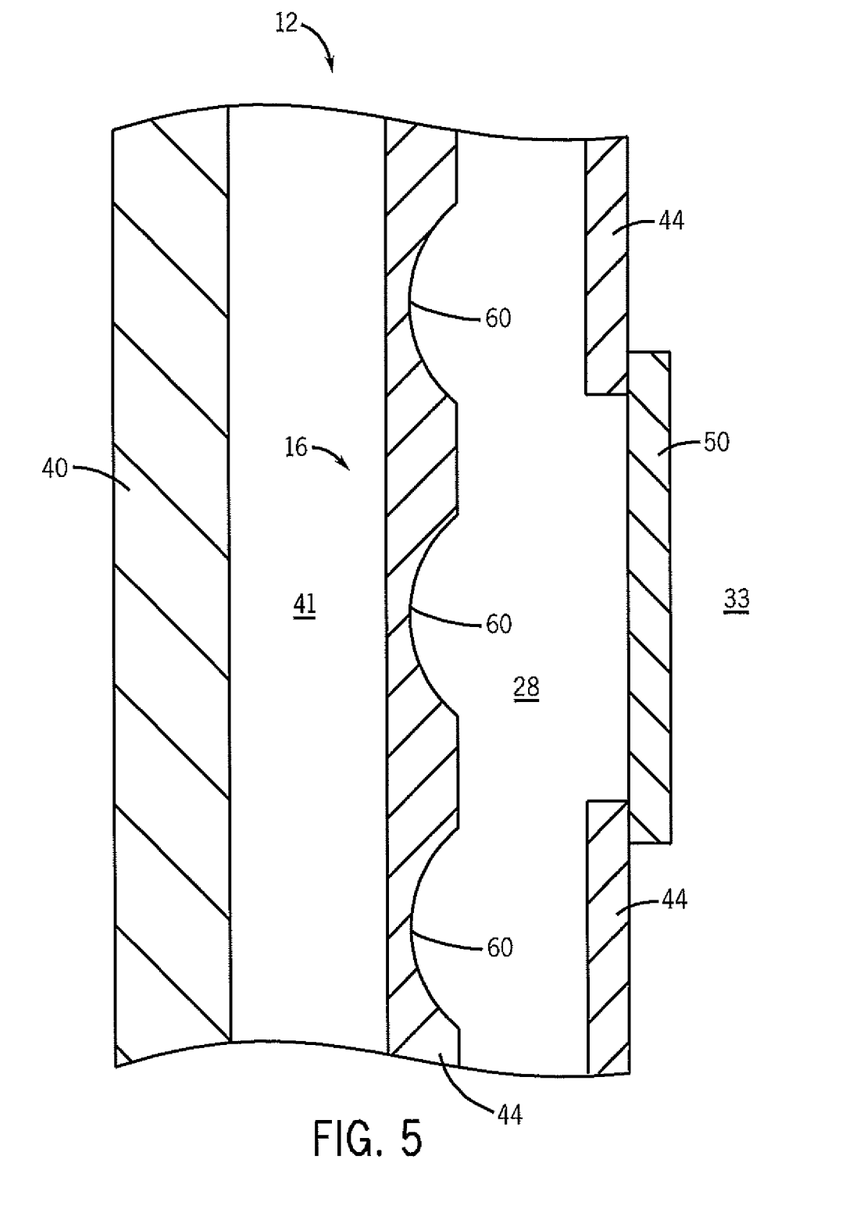
FIG. 5 is a cross-sectional view along an airway flow axis of an exemplary tracheal tube with one or more humidification lumens that include windows formed from a selectively permeable material and reservoirs for holding water vapor.

FIG. 4 is a cross-sectional view of an alternate configuration of a tube 12 along the axis of the airway flow path 33. As shown, lumens 28 may be formed from a substantially impermeable material 44 with one or more openings 49 formed on the inside surface 32 of the lumen 28. The openings 49 may be covered by a membrane formed from a selectively permeable material 50 to allow the transfer of water vapor 36 into the airway flow path 33. The openings 49 may be located at points in the flow path 33 that correspond to particular areas relative to the tracheal walls 40. For example, rather than allowing transfer of water vapor along the entire length of tube 12, which may include areas outside of the patient, the depicted configuration may allow transfer of water vapor only in certain areas, such as transfer beginning in the upper respiratory area 41 (and/or the lower respiratory area below cuff 14). Further, the depicted configuration of lumen 28 formed from substantially impermeable material 44 punctuated by openings 49, may be used in conjunction with thin membranes of selectively permeable material 50 (e.g., less than 1 mm in thickness), which may allow a faster rate of water vapor transfer. The membranes may be adhered or heat bonded over openings 49. In another embodiment, shown in FIG. 5, the lumens 28 may include reservoirs 60 formed in the lumen walls to allow more water vapor to pass through the lumen 28 for transfer into the airflow passage 33. Such reservoirs 60 may be formed during an extrusion process in which the lumens 28 are extruded into the walls 16 of the tube 12.

Further, in certain configurations, the membranes 50 may not be used and the water vapor 36 may diffuse directly into through the openings 49. Such direct diffusion may be appropriate if the rate of water vapor diffusion from the water source 30 may allow sufficient humidification without substantial loss of positive pressure through the coupling of the lumen to the water vapor source 30.

Figure 6:
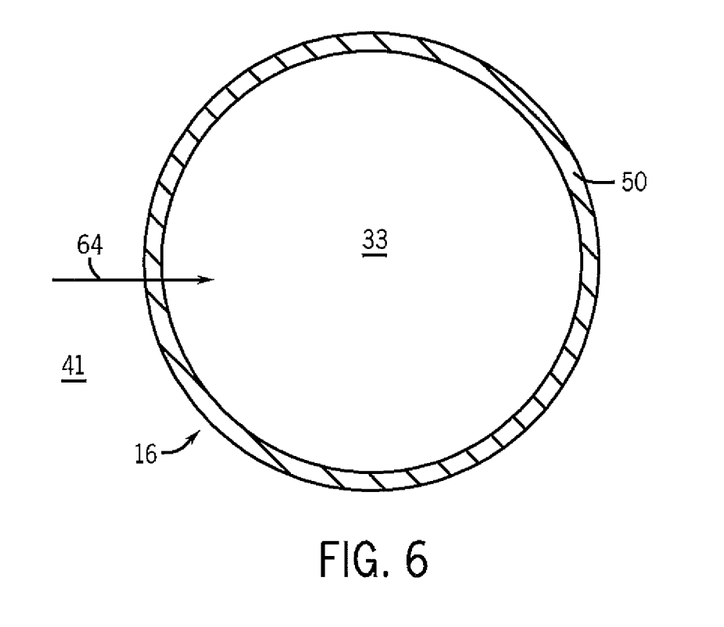
FIG. 6 is a cross-sectional view orthogonal to an airway flow axis of an exemplary tracheal tube including a passive humidification system whereby all or a portion of the walls of the tracheal tube are formed from a selectively permeable material.

In addition to active humidification in which the water vapor is provided by a water source 30, systems 10 and tracheal tubes 12 may also include passive humidification systems in which all or part of the water vapor is provided by the naturally heated and moist air of the respiratory tract. FIG. 6 is a cross-sectional view of a tube wall 16 along an axis orthogonal to the airway passage 33. As shown, the tube wall 16 is formed from a selectively permeable material 50, which allows the transfer of air 64 from the tracheal space 41 into the airflow passage.

Figure 7:
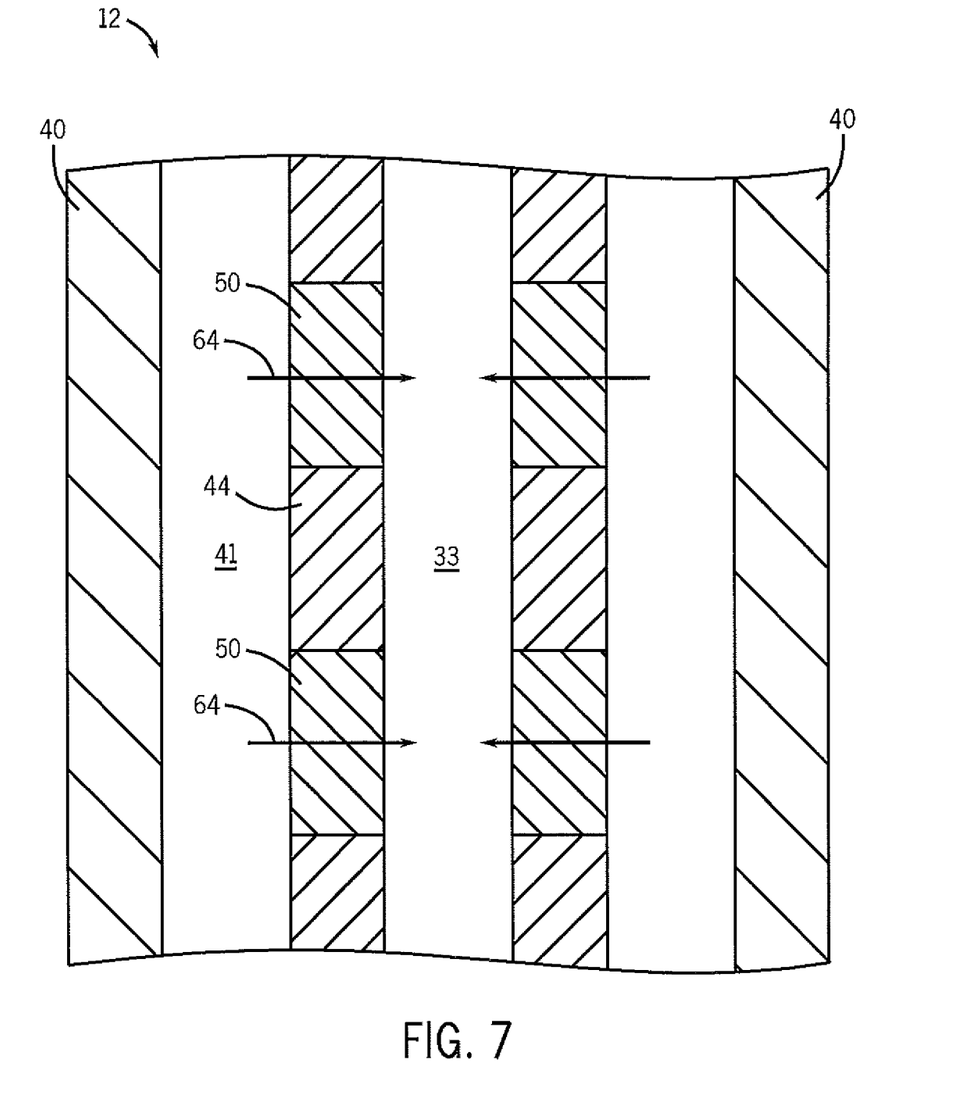
FIG. 7 is a cross-sectional view along an airway flow axis of an exemplary tracheal tube with portions of a selectively permeable material and another material.

While the entire length of the tube walls 16 may be formed from the selectively permeable material 50, in the embodiment shown in FIG. 7, the selectively permeable material 50 may form rings in the tube walls 16 that alternate with a substantially impermeable material 44. Such an implementation may reduce manufacturing costs and provide structural support for the tube 12. In other implementations, the selectively permeable material 50 may form a specific portion of the tube walls 16, such as a portion that corresponds to the inserted portion (e.g., excluding the portion that extends from the mouth of the patient).

Figure 8:
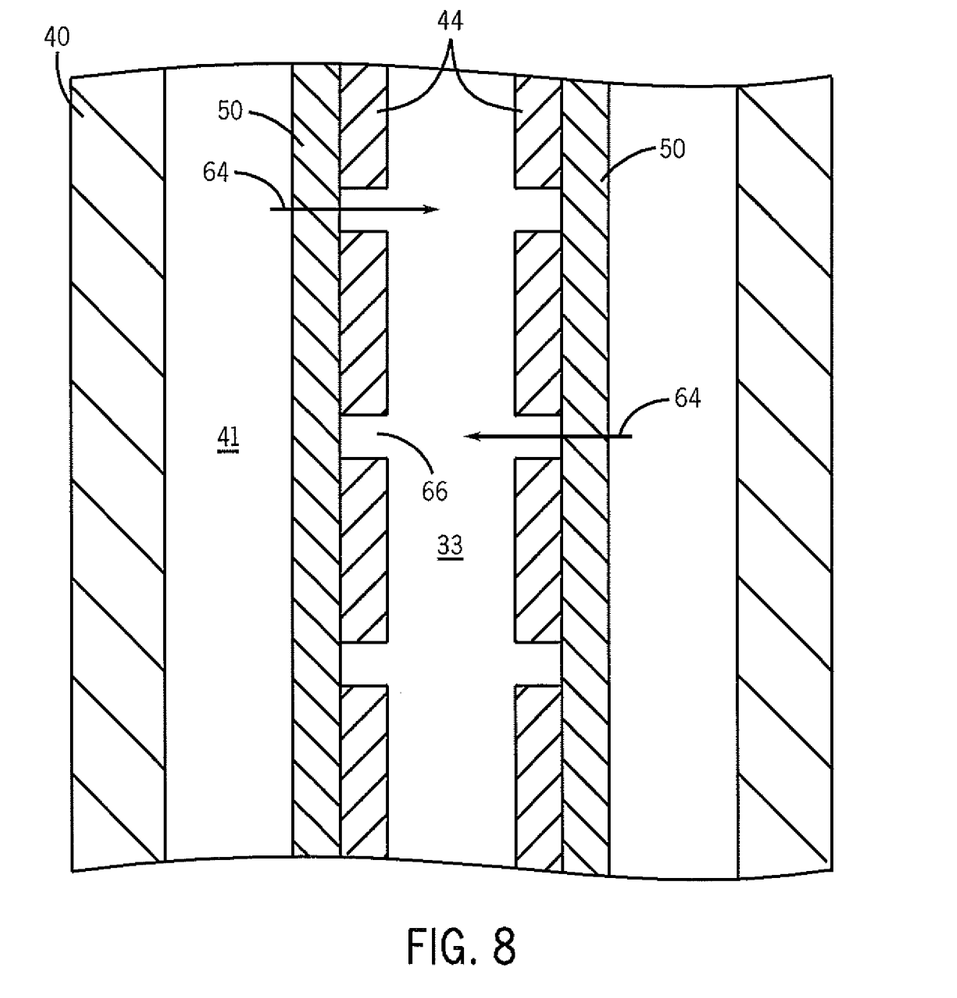
FIG. 8 is a cross-sectional view along an airway flow axis of an exemplary tracheal tube with a layer of a selectively permeable material covering windows formed in the walls of the tube.

FIG. 8 shows an exemplary tube configuration in which the tube walls 16 may be formed from a material 44 substantially impermeable to water vapor and respiratory gases. The material 44 may include one or more openings 66 that are covered by a layer of selectively permeable material 50. The selectively permeable material 50 may be coextruded as a layer over the material 44. Depending on the size of the openings, the material 50 may be relatively thin (e.g., less than about 1 mm in thickness). For larger openings, the material 50 may be thicker to provide more support.

Figure 9:
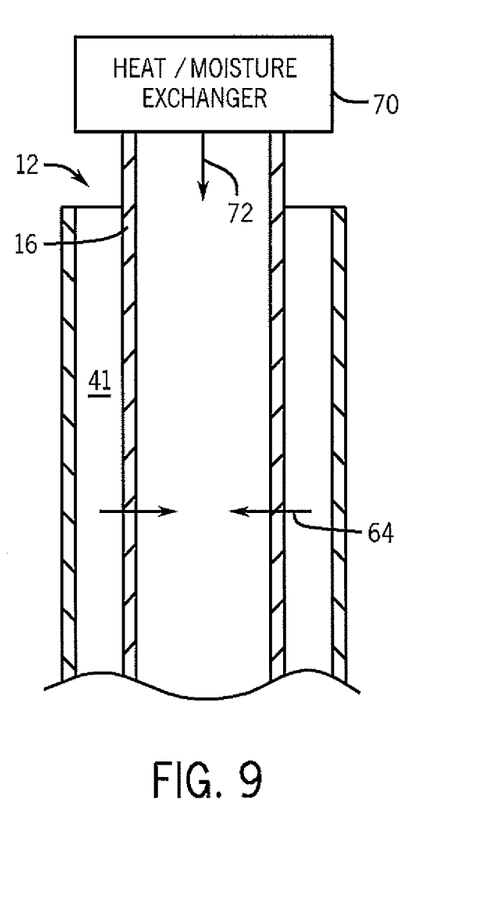
FIG. 9 is a cross-sectional view along an airway flow axis of an exemplary tracheal tube with a passive humidification system used in conjunction with a heat/moisture exchanger.

Heat and moisture exchangers are often used to provide heat and humidity to the respiratory gases entering the patient. As shown in FIG. 9, a heat and moisture exchangers 70 may be coupled to tracheal tube 12. The heat and moisture exchangers 70, often a fibrous or other gas permeable material, may accumulate heat and moisture from the exhaled gases. During inhalation, the moisturized air 72 may be recirculated. However, inefficiencies of the typical heat and moisture exchangers 70 are such that a certain portion of the heat and moisture collected is lost, for example, to the environment, rather than being passed back to the patient by exchange with respiratory gases. The moisture levels may be augmented by passive and/or active humidification systems as provided herein. For example, as shown, air 64 from the tracheal space 41 may be allowed to transfer into the tube 12 through passive humidification.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A system for airway humidification comprising:
    a tracheal tube adapted to be inserted into a patient's airway, the tracheal tube comprising;
    a first lumen configured be in-line with a breathing circuit to deliver respiratory gases, wherein the tracheal tube comprises an inner wall defining the first lumen;
    a second lumen formed within the outer wall of an tracheal tube and that is not in fluid communication with the respiratory gases, wherein the outer wall of the tracheal tube is formed from a first material impermeable to water vapor and impermeable to respiratory gases, and wherein at least a portion of the inner wall defining the first lumen comprising one or more openings covered by a second material permeable to water vapor and substantially impermeable to respiratory gases such that the second material forms a barrier between the first lumen and the second lumen along only a portion of the second lumen; and a source of water vapor in direct fluid connection with the second lumen and not the first lumen such that the water vapor transferred from the source passes through the second lumen before entering the first lumen.

2. The system of claim 1, wherein the second material comprises a fluorinated ionomer.

3. The system of claim 1, wherein the second material comprises a proton exchange membrane.

4. The system of claim 1, wherein the tracheal tube is operatively connected to a ventilator.

5. A system for airway humidification comprising:

a tracheal tube adapted to be inserted into a patient's airway for delivering respiratory gases to lungs of the patient via a first lumen within the tracheal tube, wherein at least a portion of an inner wall of the tracheal tube defining the first lumen comprises a material permeable to water vapor and substantially impermeable to respiratory gases and wherein the material forms a barrier between the first lumen and a second lumen formed within an outer wall of the tracheal tube, wherein the second lumen does not directly receive the respiratory gases; and a heat and moisture exchange device operatively connected to the tracheal tube.

6. The system of claim 5, wherein the tracheal tube is configured to allow transfer of water vapor from the patient's airway into a flow passage of the tube.

* * * * *